United States Patent
Robert et al.

(10) Patent No.: US 11,647,991 B2
(45) Date of Patent: May 16, 2023

(54) SYNTHETIC TRANSMIT FOCUSING ULTRASOUND SYSTEM WITH SPEED OF SOUND MAPPING

(71) Applicant: KONINKLIJKE PHILIPS N.V., Eindhoven (NL)

(72) Inventors: Jean-Luc Francois-Marie Robert, Cambridge, MA (US); Sheng-Wen Huang, Ossining, NY (US); Francois Guy Gerard Marie Vignon, Andover, MA (US); Jun Seob Shin, Winchester, MA (US); Seungsoo Kim, Andover, MA (US); Hua Xie, Cambridge, MA (US); Man Nguyen, Melrose, MA (US); Faik Can Meral, Mansfield, MA (US); William Tao Shi, Wakefield, MA (US); Carolina Amador Carrascal, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 52 days.

(21) Appl. No.: 17/055,300

(22) PCT Filed: May 9, 2019

(86) PCT No.: PCT/EP2019/061883
§ 371 (c)(1),
(2) Date: Nov. 13, 2020

(87) PCT Pub. No.: WO2019/219485
PCT Pub. Date: Nov. 21, 2019

(65) Prior Publication Data
US 2021/0196238 A1    Jul. 1, 2021

Related U.S. Application Data

(60) Provisional application No. 62/838,365, filed on Apr. 25, 2019, provisional application No. 62/671,488, filed on May 15, 2018.

(51) Int. Cl.
*A61B 8/08* (2006.01)
*A61B 8/00* (2006.01)
(Continued)

(52) U.S. Cl.
CPC .......... *A61B 8/5207* (2013.01); *A61B 8/4488* (2013.01); *A61B 8/461* (2013.01);
(Continued)

(58) Field of Classification Search
CPC ............ G01S 7/52049; G01S 7/52095; G01S 7/52071; A61B 8/5207
See application file for complete search history.

(56) References Cited

U.S. PATENT DOCUMENTS 4,754,760 A * 7/1988 Fukukita ............... A61B 8/5223
                                                                            600/549
5,172,343 A * 12/1992 O'Donnell ......... G01N 29/0645
                                                                            600/447

(Continued)

FOREIGN PATENT DOCUMENTS

WO    2007133879 A2    11/2007

OTHER PUBLICATIONS

International Search Report and Written Opinion for International Application No. PCT/EP2019/061883, filed May 9, 2019, 17 pages.

*Primary Examiner* — Joel Lamprecht
*Assistant Examiner* — Nyrobi Celestine

(57) ABSTRACT

In an ultrasound imaging system which produces synthetically transmit focused images, the multiline signals used to form image scanlines are analyzed for speed of sound variation, and a map 60 of this variation is generated. In a preferred implementation, the phase discrepancy of the received multilines caused by speed of sound variation in the medium is estimated in the angular spectrum domain for the receive angular spectrum. Once the phase is estimated for all
(Continued)

locations in an image, the differential phase between two points at the same lateral location, but different depth, is computed. This differential phase is proportional to the local speed of sound between the two points. A color-coded two- or three-dimensional map 60 is produced from these speed of sound estimates and presented to the user.

13 Claims, 5 Drawing Sheets

(51) Int. Cl.
  *G01S 7/52*       (2006.01)
  *G01S 15/89*      (2006.01)
(52) U.S. Cl.
  CPC .......... *A61B 8/5269* (2013.01); *G01S 7/5202* (2013.01); *G01S 7/52026* (2013.01); *G01S 7/52049* (2013.01); *G01S 7/52071* (2013.01); *G01S 15/8915* (2013.01); *A61B 8/0891* (2013.01)

(56) References Cited

U.S. PATENT DOCUMENTS

| | | | | |
|---|---|---|---|---|
| 5,268,876 A | | 12/1993 | Rachlin | |
| 5,348,013 A | * | 9/1994 | Kanda | G01S 7/52026 600/443 |
| 5,921,932 A | * | 7/1999 | Wright | G10K 11/345 600/447 |
| 5,928,152 A | * | 7/1999 | Wright | G10K 11/346 600/447 |
| 5,935,068 A | * | 8/1999 | Zhu | G01H 3/125 600/458 |
| 6,432,056 B1 | * | 8/2002 | Cooley | G01S 7/52095 600/443 |
| 7,828,731 B2 | * | 11/2010 | Baba | G06T 7/32 600/443 |
| 8,137,272 B2 | * | 3/2012 | Cooley | G01S 7/52028 600/463 |
| 2003/0100833 A1 | * | 5/2003 | He | G01S 7/52082 600/453 |
| 2005/0148874 A1 | | 7/2005 | Brock-Fisher et al. | |
| 2005/0288583 A1 | * | 12/2005 | Hirota | A61B 8/12 600/437 |
| 2006/0106309 A1 | * | 5/2006 | Liu | G01S 7/52095 600/447 |
| 2008/0114255 A1 | * | 5/2008 | Schwartz | A61B 8/4483 600/474 |
| 2009/0141957 A1 | * | 6/2009 | Yen | G01S 15/8977 600/437 |
| 2009/0326377 A1 | * | 12/2009 | Hirama | G01S 15/8927 600/447 |
| 2012/0165670 A1 | * | 6/2012 | Shi | A61B 5/6814 600/442 |
| 2014/0371774 A1 | * | 12/2014 | Hwang | A61B 8/5261 606/169 |
| 2018/0125451 A1 | | 5/2018 | Duncan et al. | |

\* cited by examiner

SYNTHETIC TRANSMIT FOCUSING ULTRASOUND SYSTEM WITH SPEED OF SOUND MAPPING

RELATED APPLICATION

This application is a U.S. National Phase application under 35 U.S.C § 371 of International Application No. PCT/EP2019/061833, filed on May 9, 2019, which claims priority to and the benefit of U.S. Provisional Application Nos. 62/671,488, filed May 15, 2018, and 62/838,365, filed Apr. 25, 2019, which are incorporated by reference in their entireties.

TECHNICAL FIELD

This invention relates to ultrasound imaging systems and, in particular, to ultrasound imaging systems which produce a map of speed of sound variation in an ultrasound image which is synthetically transmit focused.

BACKGROUND

Conventional ultrasound systems are dynamically focused during echo signal reception by continually adjusting the delays used to combine echoes from different transducer elements across the aperture as the echoes are received from increasing depths of field. Thus, the received signals are properly focused at all depths of field. But on transmit, the transmitted beam can only be focused at a single focal depth; once the transmit beam is launched into the body, it cannot be further modified. Consequently, the transmit beam is only fully focused at a single depth of field, as compared to the received beam which is focused at all depths. Since the full focal characteristic is a product of both the transmit focus and the receive focus, the resultant image is most sharply focused only at the transmit focal depth.

U.S. Pat. No. 8,137,272 (Cooley et al.) describes a technique for processing multiple receive beams to synthesize echo signals which have the characteristic of being transmit focused at all depths. As described in this patent, a multiline beamformer produces a plurality of adjacent receive lines in response to each transmit beam. The receive lines from successive transmission from different points along the aperture are in spatial alignment, so that a plurality of lines are received from different transmit events at each line location. The lines from a common spatial location are weighted and delayed, and then combined with a phase adjustment to account for the different round trip times of echoes from the differently located transmit beams. The combined multilines then have the characteristic of scanlines that were continually focused during transmission, producing a sharper image over the full depth of field.

However, the weights and delays used to accurately beamform and then combine the received multilines at each line location are premised on an assumed constant speed of travel of the echoes in the medium, generally assumed to be the average speed of sound in tissue, e.g., 1450 m/sec. But this assumption is not always accurate, as different types of tissue and tissue density can cause traveling ultrasound waves to exhibit velocities different than the assumed speed. Thus, there can be inaccuracies in forming and combining the multilines as desired.

SUMMARY

The present invention involves detecting and displaying such speed of sound aberrations to the user, such as by means of a two or three-dimensional map of the speed of sound variation across the imaged region.

In accordance with the principles of the present invention, the multiline signals used to form synthetically focused ultrasound scanlines are analyzed for speed of sound variation, and a map of this variation is generated and presented to the user. In a preferred implementation, the phase discrepancy of the received multilines caused by speed of sound variation in the medium is estimated in the angular spectrum domain for the receive angular spectrum. Once the phase is estimated for all locations in an image, the differential phase between two points at the same lateral location, but different depth, is computed. This differential phase is proportional to the local speed of sound between the two points. A color-coded two- or three-dimensional map of the image area is produced from these speed of sound estimates and presented to the user.

Figure 1A:
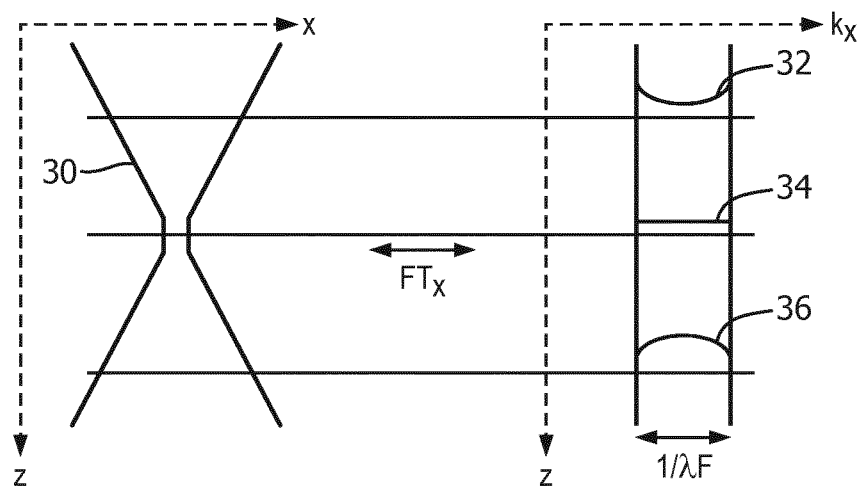
FIGS. 1a and 1b illustrate the signal phase with aberration and without aberration, respectively.

Referring first to FIG. 1a, the left side of the drawing illustrates the beam profile 30 of a statically focused ultrasound beam. As the beam profile illustrates, the beam is maximally focused only at one depth where the profile is at its narrowest. The right side of the drawing illustrates the phase of the angular spectrum of the beam, the Fourier transform across the beam profile. The phase variation across the beam focus is represented by line 34, and is seen to be flat at the focus. Above and below the focal point, at shallower and deeper depths, the phase variation is seen to be spherical, as represented by curves 32 and 34.

Figure 1B:
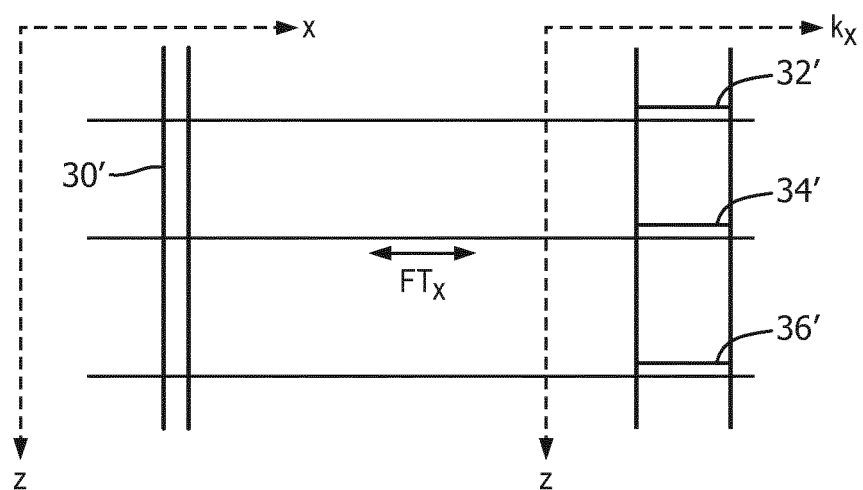

FIG. 1b illustrates the phase of the angular spectrum for an ultrasound beam 30' that is dynamically focused at all depths. In this case the phase variation of the angular spectrum is flat at all depths, as indicated by lines 32', 34', and 36'. In the absence of speed of sound variation in the medium, the pre-computed coefficients used for dynamic transmit focusing will produce beams with this phase characteristic. But speed of sound variation in the medium will cause defocusing rather than sharp focusing at all depths. It is an object of the present invention to detect and cancel phase aberrations that would detract from the desired flat phase characteristic of the angular spectrum of dynamically focused ultrasound beams.

Figure 2:
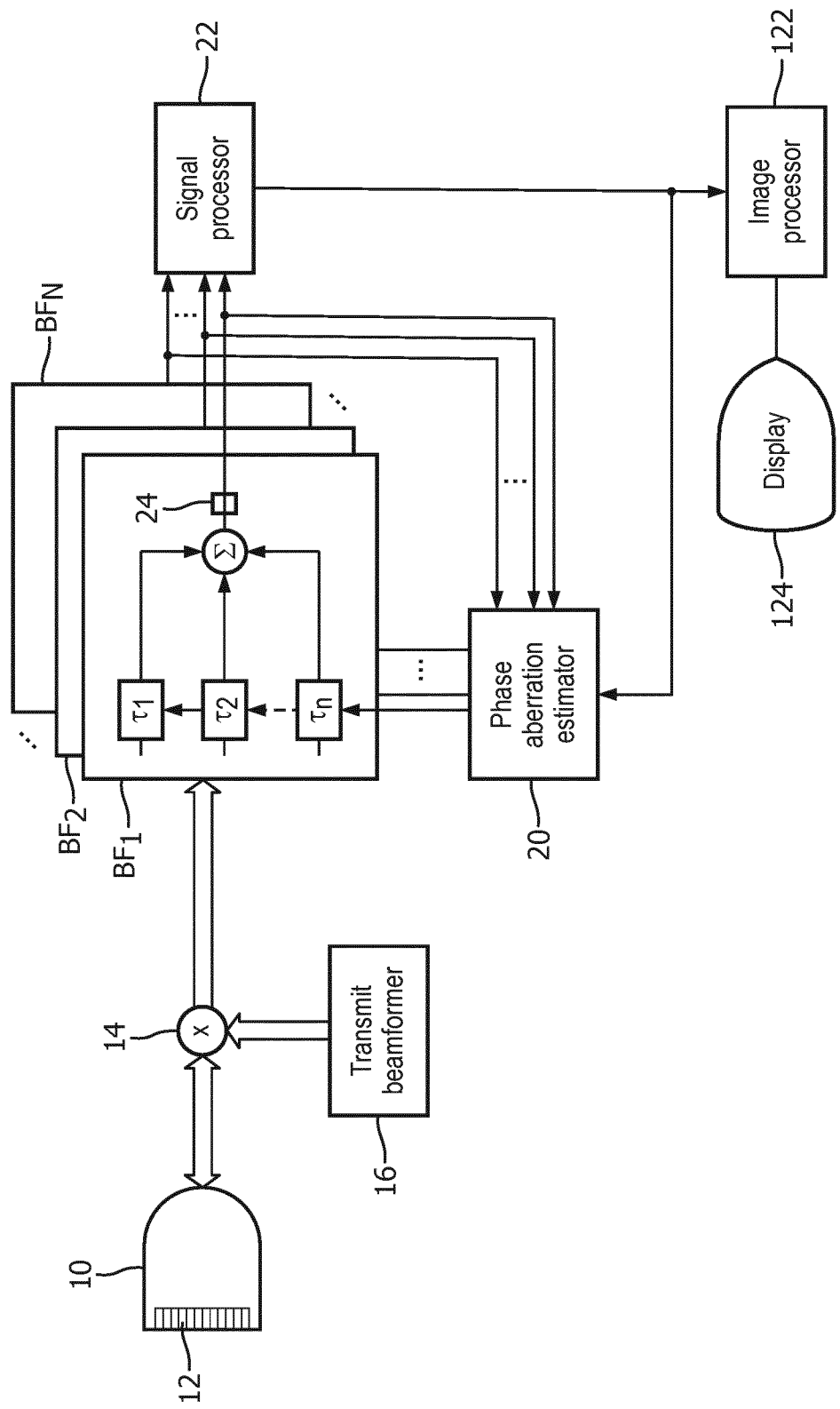
FIG. 2 illustrates in block diagram form an ultrasound system constructed in accordance with the present invention.

In FIG. 2 an ultrasonic imaging system constructed in accordance with the principles of the present invention is shown in block diagram form. A transducer array 12 is provided in an ultrasound probe 10 for transmitting ultrasonic waves and receiving echo signals. The transducer array 12 may be a one- or two-dimensional array of transducer elements capable of scanning in two or three dimensions, for instance, in both elevation (in 3D) and azimuth. A transmit beamformer 16 is coupled to the elements of the array to excite elements of the active transmit aperture at appropriate times to transmit a beam of a desired shape and direction. For multiline reception the transmit beam is broadly shaped so as to insonify a plurality of receive beam locations in the image field. Among the transmit characteristics controlled by the transmit beamformer are the number, direction, spacing, amplitude, phase, frequency, polarity, and diversity of transmit waveforms. Beams formed in the direction of pulse transmission may be steered straight ahead from the transducer array, or at different angles on either side of an unsteered beam for a wider sector field of view. For some applications, unfocused plane waves may be used for transmission.

The probe 10 is coupled by means of transmit/receive switches 14, which protect the receive beamformer from high voltage transmit signals, to a receive beamformer. For multiline reception the echo signals received by elements of the array 12 are beamformed in parallel by appropriately delaying them and then combining them in multiline sub-beamformers $BF_1$, $BF_2$, ... $BF_N$, which together comprise a multiline beamformer. Each sub-beamformer has differently programmed delays $\tau_1 \ldots \tau_n$ followed by a summer E which produce steered and focused receive beams at different locations of an image field. The multiline beamformer is thus capable of forming N receive beams in parallel in response to echoes received in a single transmit event, and uses this capability to form N adjacent receive lines in response to one transmit beam. For synthetic transmit focusing the transmit beams are progressively shifted across the probe aperture, but each set of receive lines is aligned with the locations of receive lines of other transmit events. The result is that multiple receive lines are produced at each receive line location from multiple, spatially offset transmit beams. The receive lines of each receive line location are then processed together as described below to form a single receive line for imaging which is synthetically transmit-focused.

The outputs of the multiline beamformer are coupled to a signal processor 22 where the coherent echo signals may undergo signal processing such as noise filtering or noise reduction as by spatial or frequency compounding. The processed signals are coupled to an image processor 122 for processing such as B mode detection and scan conversion, and the resultant images are displayed on a display 124.

Figure 2A:
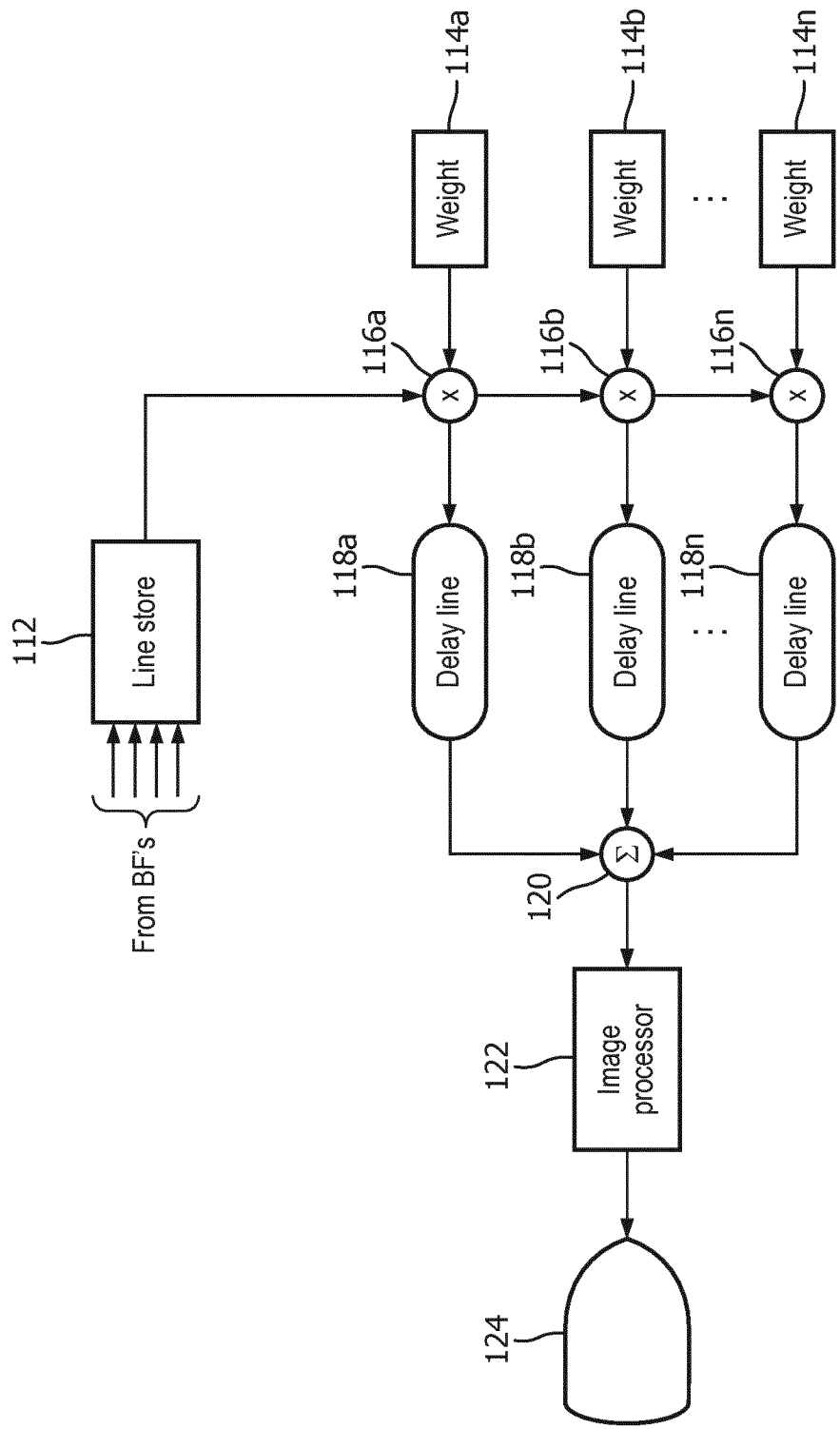
FIG. 2a illustrates synthetic transmit focusing circuitry which is included in the signal processor of FIG. 2.

For synthetic transmit focusing the signal processor 22 also comprises circuitry as shown in FIG. 2a. The received multilines produced by the multiline beamformer are buffered in a line store 112 so that receive lines received at the same line location at different times may be processed in parallel. A group of multilines used to form a particular line of display data are applied to respective ones of multipliers 116a-116n to produce the display data for the corresponding line location. The echo data from each line may, if desired, be weighted by apodization weights 114a-114n. In general, these weights will weight each multiline as a function of its round-trip impulse response. A suitable weighting algorithm can be derived by letting the term amplitude (x, z) be the insonification amplitude of a point at location (x, z) in the image field by the transmit wavefront, the azimuth position x=0 corresponding to the center axis of the transmit beam. Let X be the azimuth of the received multiline with respect to the transmit beam axis. The weight applied to this received multiline to form a point of the image at depth Z is:

Weight(X,Z)=amplitude(X,Z)

For determination of an appropriate delay characteristic, let propagation_time (x, z) be the propagation time needed by the transmit wavefront to reach a point at location (x, z), the azimuth x=0 corresponding again to the center axis of the transmit beam. Let X be the azimuth of the receive line with respect to the transmit beam axis. The delay applied to this received multiline to form a point of the image at depth Z is:

Delay(X,Z)=propagation_time(X,Z)−propagation_time (0,Z)

where propagation_time (0, Z) is the time to reach a point at the same depth but on-axis.

The functions amplitude (X, Z) and propagation_time (X, Z) may, for example, be obtained from a simulation of the transmit field. An appropriate way to compute the propagation time is to use the phase delay of the field from monochromatic simulation at several frequencies. The amplitude may be computed by averaging the amplitude of the field at several frequencies. In addition, a depth-dependent normalization can be applied to the weights. This multiplies all the weights at a given depth by a common factor. For example, the normalization can be chosen so that speckle regions have uniform brightness with depth. By varying the weights as a function of depth, it is possible to vary the size and shape (apodization) of the aperture dynamically with depth.

The amplitude and propagation time do not need to be derived from a simulation of the exact transmit characteristics used in the system. The designer may choose to use a different aperture size or a different apodization, for example.

The echoes from each line are weighted by the multipliers 116a-116n and delayed by delay lines 118a-118n. In general, these delays will be related to the location of the transmit beam center to the receive line location. The delays are used to equalize the phase shift variance that exists from line to line for the multilines with differing transmit-receive beam location combinations, so that signal cancellation will not be caused by phase differences of the combined signals. The delayed signals are combined by a summer 120 and the resultant signals are coupled to the image processor 122.

In the system of FIG. 2a the delay lines 118 and summer 120 effect a refocusing of the signals received from the several receive multilines which are co-aligned in a given direction. The refocusing adjusts for the phase differences resulting from the use of different transmit beam locations for each multiline, preventing undesired phase cancellation in the combined signals. The weights 114 weight the contributions of the multilines in relation to the proximity of the transmit beam to the multiline location, giving higher weight to receive beams with higher signal-to-noise ratios. This results in an extended depth of field along each receive line and an enhanced penetration (improved signal-to-noise ratio) due to the combination of multiple samplings in each receive line direction.

In accordance with the principles of the present invention, the ultrasound system of FIG. 2 further comprises a phase aberration estimator 20. The present inventors have determined that beam defocusing is caused by aberrations of the phase term of the angular spectrum. Accordingly, the phase aberration estimator estimates this phase term and then corrects it. Preferably this is done for both transmit and receive, using the appropriate datasets of the received multiline data.

The processing performed by the phase aberration estimator 20 proceeds as follows. First, the angular spectrum in transmit is computed. This is done by taking a two-dimensional Fourier transform of the multiline dataset for each line location, the multilines corresponding to the same line location. The phase aberration estimator acquires this data by its connections to the outputs of the sub-beamformers $BF_1 \ldots BF_N$ as shown in the drawing. This dataset has the dimensions of depth and transmit, since each multiline at the common location was acquired during a different transmit event. In a constructed implementation, each multiline was divided into successive 5 mm depth zones and the angular spectrum computed for each zone. Since the data has been converted to the frequency domain by Fourier transformation, the phase of the angular spectrum can be estimated at each kx spatial frequency in the kx band. The cross-correlation function of the angular spectrum between spatial frequencies kx(n) and kx(n+1) is computed by:

$$\rho_{kz,kx(n)kx(n+1)} = S(kz,kx(n)) * \overline{S(kz,kx(n+1))} \tag{1}$$

where S is the angular spectrum of the multiline data in the depth (z) and transmit (x) dimensions, and n and (n+1) are adjacent pixels in the frequency domain.

Since ultrasound signals are coherent, ultrasound images are contaminated by an artifact phenomenon known as speckle, which results from the random cancellation and reinforcement of acoustic signal in the imaging medium. To minimize the effect of the speckle artifact on the aberration estimation, the speckle is smoothed by averaging. A suitable equation for speckle smoothing is:

$$\overline{\rho}_{kx(n)kx(n+1)} = \frac{\sum_{i=1}^{N} \rho^{i}_{kx(n)kx(n+1)}}{N} \tag{2}$$

which averages the speckle effect on the correlation coefficient over N multilines, where N is the number of received multilines to be averaged and $\rho_{kx(n)kx(n+1)}^{i}$ is the cross-correlation function of the angular spectrum between spatial frequencies kx(n) and kx(n+1). The differential phase of the averaged correlation function of adjacent frequencies between spatial frequencies kx(n) and kx(n+1) is computed as:

$$\Delta\varphi_{kx(n)kx(n+1)} = \angle \overline{\rho}_{kx(n)kx(n+1)} \tag{3}$$

The differential phase values are then integrated to yield the absolute phase over the entire range of kx spatial frequencies:

$$\varphi_{kx(n)} = \sum_{i=0}^{n-1} \Delta\varphi_{kx(i)kx(i+1)} \tag{4}$$

The phase term will include the effect of beam steering, which is not to be affected by the aberration correction process. To prevent this, the linear trend of the phase term is removed by a detrending process. Known detrending techniques may be used for this process. The phase term is then averaged along temporal frequencies, using the assumption that the phase varies linearly as a function of the frequency k. This may be done by scan converting the phase from its (kz, kx) coordinates to (k, theta) coordinates, where $k^2 = kx^2 + kz^2$ is the temporal frequency and theta represents a plane wave angle. Alternatively, this may be accomplished by averaging along kz. The resultant estimated phase term is then used to remove the phase of the angular spectrum. This is done by transforming the phase estimate from its vector form after averaging, $\varphi(kx)$, to its matrix form, $\varphi(kx, kz)$, and multiplying the angular spectrum by $G = e^{-i\varphi(kx, kz)}$ where $\varphi(kx, kz)$ is the estimated phase. An inverse two-dimensional Fourier transform is then applied to return the data to spatial coordinates. Alternatively, a matched filter 24 may be used at the beamformer outputs to cancel the aberrating phase term from the multiline signals.

The same process is used for aberration phase estimation and correction in receive, but using a different dataset. The receive dataset is a set of multilines received in response to a single transmit event. For this purpose the multilines used may be ones which have undergone synthetic transmit focus processing by the FIG. 2a circuitry. Thus, a connection is shown between the signal processor 22 and the phase aberration estimator 20 to provide this data. The two-dimension Fourier transformation of the first processing step is then done in the depth and receive dimensions. The phase term for receive aberration is then computed and used to correct the data as explained above for the transmit case.

Figure 3:
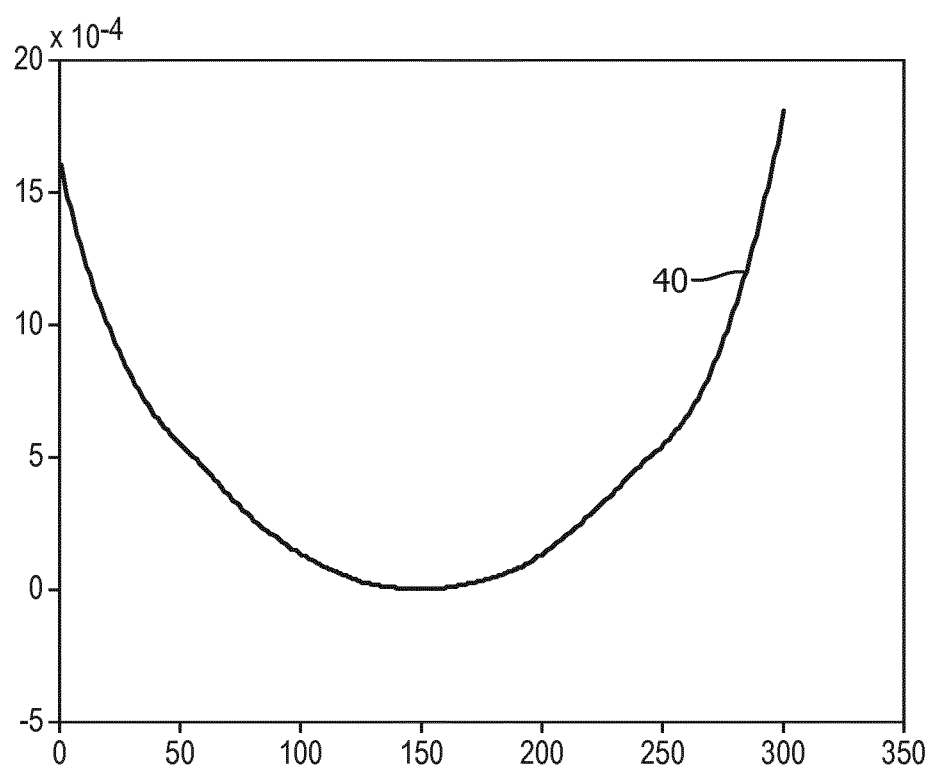
FIG. 3 is a plot of spherical aberration phase effects which were detected by a constructed implementation of the present invention.

Since the receive phase correction operates on multiline data which has already undergone dynamic focusing by the circuitry of FIG. 2a, its expected phase terms, in the absence of speed of sound aberration, should be flat at all depths, as illustrated by 32', 34' and 36' in FIG. 1b. The transmit phase correction, which was seen to operate on multilines produced at the outputs of the sub-beamformers, is different. Its expected phase terms are flat at the focal depth and spherical at other depths, as shown by 32, 34, and 36 of FIG. 1a. FIG. 3 illustrates a transmit phase estimate curve 40 after detrending and averaging by a constructed implementation of the present invention, and is seen to exhibit the expected spherical shape for a depth shallower than the focal depth of a transmit beam.

Estimation of the aberrating phase and its compensation may be performed in an implementation of the present invention entirely in the spatial domain as follows. For the transmit phase estimation and correction, the cross correlation is estimated between the multiline data of adjacent transmit beams b(n) and b(n+1) for a common receive line location:

$$\rho_{b(n)b(n+1)}(l) = \sum_{k=k_{min}}^{k_{max}} (b(k, n) \times b(k+l, n+1)) \tag{5}$$

where the multiline data is in the depth and transmit dimensions. To smooth speckle noise, the correlation function is averaged over multiple receive lines as well as multiple depth samples:

$$\overline{\rho}_{b(n)b(n+1)}(l) = \frac{\sum_{i=1}^{N} \rho^{i}_{b(n)b(n+1)}(l)}{N} \tag{6}$$

where N is the total number of receive lines and depth samples and $\rho_{b(n)b(n+1)}^{i}(l)$ is the $i^{th}$ cross correlation function between transmit beams b(n) and b(n+1). The differential delays between adjacent transmit lines is then calculated by:

$$\Delta d_{b(n)b(n+1)} = l |_{max(\overline{\rho}_{b(n)b(n+1)}(l))} + \Delta l$$

where $\Delta l$ is a fine delay obtained by sub-pixel estimation (interpolation) and l is the index corresponding to the function maximum.

The differential delays from lines of different transmits are integrated to yield an absolute delay value:

$$d_{b(n)} = \sum_{i=0}^{n-1} \Delta d_{b(i)b(i+1)} \tag{8}$$

A detrending technique is applied as discussed above to remove the first order term of the delay to avoid affecting the intended beam steering. The compensated delays are then used by delay lines 118a . . . 118n to remove the phase aberration during the synthetic transmit focusing process.

The same process is used for receive delay correction using the receive dataset described above.

As long as the aberration is a speed of sound error, only the phase of the angular spectrum is affected. For other aberrators, the amplitude may also be affected. Simply correcting the phase can still improve the focusing, but a better correction can be obtained if the amplitude is also compensated such as by inverse filtering. A Weiner filter can serve this purpose. A Weiner filter for gain applied to the angular spectrum prior to two-dimensional inverse Fourier transformation is given by:

$$G = Ae^{-i\varphi} \frac{S}{A^2 S + N} \quad [9]$$

where A is the estimated amplitude of the angular spectrum, S is the signal level, N is the noise level, and $\varphi$ is the (absolute) phase correction. If the signal-to-noise ratio is infinite, then the filter operates as an inverse filter; if there is noise, the Wiener filter will prevent amplification of small noise coefficients.

The foregoing techniques for estimating the speed of sound at points in an image can be applied to produce a map of speed of sound variation over the full image field. Local speed of sound measurement can provide information on the tissue type. For example, this information can help differentiate between healthy and fatty liver tissue. This would provide important information for the screening of non-alcoholic fatty liver disease (NAFLD) and non-alcoholic steato hepatitis (NASH), for instance. Production of a speed of sound map begins by estimating the phase in the angular spectrum domain as explained above. Preferably, the phase estimation is done using the receive data described above, since this data has undergone synthetic transmit focus processing using the circuitry of FIG. 2a, and in the absence of speed of sound variation the phase should be flat as shown in FIG. 1b. If desired, the transmit speed of sound correction can be performed as described above, which results in a better phase estimation in receive. Thus, if the receive point spread function is perfectly focused, the phase of the angular spectrum on receive should be perfectly flat. Speed of sound variation will result in local defocusing and a spherical phase characteristic as shown in FIG. 1a.

The phase error for an angular frequency corresponding to plane wave angle $\theta$ which is related to the spatial frequency through theta=arctan (kx/kz) is $$\frac{2\pi}{\lambda} \cos(\theta) z_0 \left( \frac{c}{c_0} - \frac{c_0}{c} \right) \quad [10]$$

where $\lambda$ is the wavelength of the ultrasound transmit frequency, $z_0$ is depth, $c_0$ is the nominal speed of sound in the absence of variation, and c is the actual speed of sound at the location in question. After averaging over the frequency range of the transmit beam and fitting by a least mean square method over a range of $\cos(\theta)$ angles, the estimate of the phase curvature can be calculated as $$Coef = 2\pi \Delta z_0 \left( \frac{c}{c_0} - \frac{c_0}{c} \right) = 2\pi \Delta z_0 \frac{c^2 - c_0^2}{c \cdot c_0} \quad [11]$$

When $$\alpha = \frac{Coef}{2\pi \Delta z}$$

this leads to $$\alpha = \frac{c^2 - c_0^2}{c \cdot c_0}$$

and multiplying both sides of the equation by ($c \cdot c_0$) leads to a second order equation of the speed of sound as $$c^2 - \alpha \cdot c \cdot c_0 - c_0^2 = 0 \quad [12]$$

A first order solution in terms of $\alpha$ is $$C = C_0 \left( 1 + \frac{\alpha}{2} \right) \quad [13]$$

and the full solution is $$C = C_0 \left( 1 + \frac{\alpha}{2} + \frac{\alpha^2}{8} \right) \quad [14]$$

To get accurate phase estimation in speckle, one needs to average on an area. Suitable areas are slices of 1 mm in depth, and 32 transmit lines laterally. The phase for receive data described above is estimated over the image area using equations [1]-[4]. Once the phase is estimated at all points in an image, the differential phase between points at the same lateral location but different depths is computed. This differential phase is proportional to the local speed of sound between the two points. The differential phase is then fitted using a least mean square estimator to find the local curvature of the phase. The values of the speed ma are given by $$C = C_0 \left( 1 + \frac{\alpha}{2} \right) \quad [15]$$

where $$\alpha = \frac{Coef}{2\pi \Delta z},$$

The phase curvature is related to the actual speed of sound of the medium, either curved as shown in FIG. 1a when there is a speed of sound difference or flat as shown in FIG. 1b in the absence of speed of sound variation. The differential phase values are converted to color values by a look-up table and are displayed as a color map that illustrates speed of sound variation in the image field.

Figure 4:
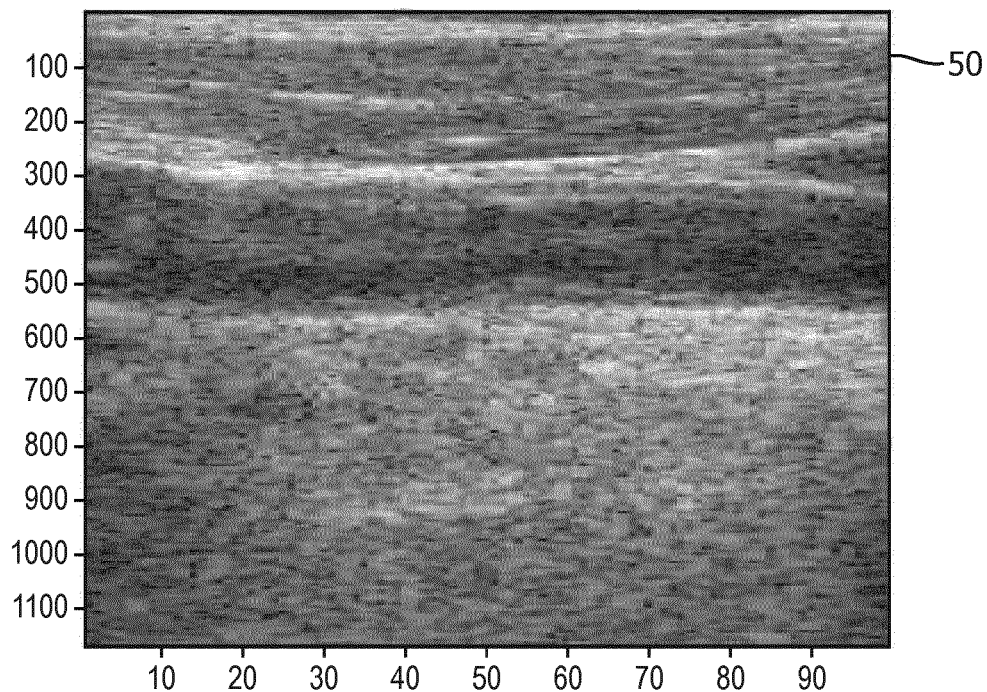
FIG. 4 illustrates an ultrasound image of a carotid artery.
Figure 5:
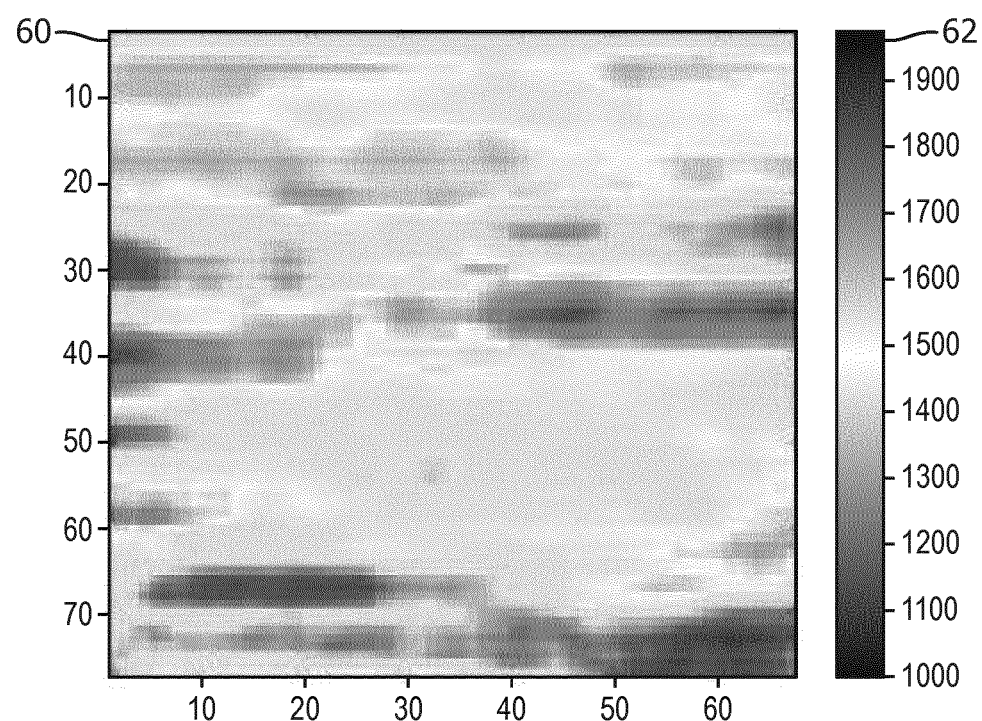
FIG. 5 illustrates a speed of sound map for the area of the ultrasound image of FIG. 4.

FIG. 4 illustrates an ultrasound image 50 of a carotid artery in vivo. FIG. 5 illustrates a speed of sound map 60 computed for this image region. The color bar 62 to the right of the map relates the colors of the map to actual speed of sound velocities in the anatomy of FIG. 4.

It should be noted that an ultrasound system suitable for use in an implementation of the present invention, and in particular the component structure of the ultrasound system of FIGS. 2 and 2a, may be implemented in hardware, software or a combination thereof. The various embodiments and/or components of an ultrasound system, or components and controllers therein, also may be implemented as part of one or more computers or microprocessors. The computer or processor may include a computing device, an input device, a display unit and an interface, for example, for accessing the internet. The computer or processor may include a microprocessor. The microprocessor may be connected to a communication bus, for example, to access a PACS system or the data network for importing training images. The computer or processor may also include a memory. The memory devices such as ones used for the line store 112 may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" or "workstation" may include any processor-based or microprocessor-based system including systems using microcontrollers, reduced instruction set computers (RISC), ASICs, logic circuits, and any other circuit or processor capable of executing the functions and equations described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions of an ultrasound system including those controlling the acquisition, processing, and display of ultrasound images as described above, and in particular the functioning of the phase aberration estimator and speed of sound mapping, may include various commands that instruct a computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules such as a transmit control module, and aberration correction module, a program module within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasound imaging system which maps speed of sound variation in an image field comprising:
    a transducer array probe;
    a transmit beamformer coupled to the transducer array probe and adapted to control the transducer array probe to transmit a plurality of transmit beams that are spatially offset from one another;
    a multiline beamformer coupled to the transducer array probe and adapted to produce a first plurality of multilines associated with each transmit beam of the plurality of transmit beams;
    synthetic transmit focusing circuitry coupled to the multiline beamformer and adapted to receive the first plurality of multilines lines and perform synthetic transmit focus processing on the first plurality of multilines to produce a second plurality of multilines that has undergone the synthetic transmit focus processing, wherein the second plurality of multilines are associated with different transmit beams of the plurality of transmit beams, wherein the second plurality of multilines are aligned at a receive line location such that the second plurality of multilines correspond to a synthetic transmit-focused receive line at the receive line location;
    a phase aberration estimator coupled to the synthetic transmit focusing circuitry and adapted to:
        estimate phase variation at the receive line location using the second plurality of multilines, the phase variation corresponding to a variation in phase of an angular spectrum in a frequency domain at the receive line location; and
        produce a map of the phase variation, wherein the map of the phase variation is different than an ultrasound image of the image field; and
    a display coupled to the phase aberration estimator and adapted to display the map of the phase variation.

2. The ultrasound imaging system of claim 1, wherein the phase aberration estimator is further adapted to take a two-dimensional Fourier transform of the second plurality of multilines in order to derive the angular spectrum in the frequency domain.

3. The ultrasound imaging system of claim 2, wherein the phase aberration estimator is further adapted to estimate the phase of the derived angular spectrum.

4. The ultrasound imaging system of claim 3, wherein the phase aberration estimator is further adapted to calculate a cross correlation function of the angular spectrum between different spatial frequencies.

5. The ultrasound imaging system of claim 4, wherein the phase aberration estimator is further adapted to smooth image speckle by averaging.

6. The ultrasound imaging system of claim 4, wherein the phase aberration estimator is further adapted to integrate differential phase values to yield absolute phase over a range of spatial frequencies.

7. The ultrasound imaging system of claim 6, wherein the phase aberration estimator is further adapted to average the absolute phase along temporal frequencies.

8. The ultrasound imaging system of claim 7, wherein the phase aberration estimator is further adapted to use the absolute phase to remove the phase of the angular spectrum.

9. The ultrasound imaging system of claim 5, wherein the phase aberration estimator is further adapted to compute differential phase between points at different depths in the image field.

10. The ultrasound imaging system of claim 5, wherein the phase aberration estimator is further adapted to compute differential phase between points at the same lateral location but at different depths in the image field.

11. The ultrasound imaging system of claim 9, wherein the phase aberration estimator is further adapted to fit the differential phase using a least mean square estimator to find a local curvature of the phase.

12. The ultrasound imaging system of claim 11, wherein the phase aberration estimator is further adapted to convert values of the differential phase to color values using a look-up table.

13. The ultrasound imaging system of claim 12, wherein the phase aberration estimator is further adapted to form a color map of the color values for display.

\* \* \* \* \*